United States Patent [19]

Tungate

[11] Patent Number: 5,080,095
[45] Date of Patent: Jan. 14, 1992

[54] UNIVERSAL ICE-PACK HOLDER FOR APPLICATION TO JOINTS AND MUSCLES

[76] Inventor: Michael D. Tungate, 2206 Quarry Cir., East Lansing, Mich. 48823

[21] Appl. No.: 510,618

[22] Filed: Apr. 19, 1990

[51] Int. Cl.$^5$ .............................................. A61F 7/00
[52] U.S. Cl. .................................. 128/402; 383/901
[58] Field of Search ............. 128/402, 403, 400, 379, 128/380, 157, 165, 77; 82/530; 383/901

[56] References Cited

U.S. PATENT DOCUMENTS

| | | | |
|---|---|---|---|
| 3,480,012 | 11/1969 | Smithers et al. | 128/165 |
| 3,491,761 | 1/1970 | Baker | 128/402 |
| 3,561,442 | 2/1971 | Goswitz | 128/157 |
| 3,880,161 | 4/1975 | Fossel | 128/165 |
| 3,888,244 | 6/1975 | Lebold | 128/77 |
| 3,889,684 | 6/1975 | Lebold | 128/402 |
| 4,033,354 | 7/1977 | De Rosa | 128/402 |
| 4,548,212 | 10/1985 | Leung | 128/402 |
| 4,585,003 | 4/1986 | Meistrell | 128/402 |
| 4,693,241 | 9/1987 | Trznadel | 128/157 |
| 4,777,946 | 10/1988 | Watanabe et al. | 128/157 |

Primary Examiner—Edward M. Coven
Assistant Examiner—Mark S. Graham
Attorney, Agent, or Firm—Harness, Dickey & Pierce

[57] ABSTRACT

A universal ice-pack holder for removably holding an ice-pack or like device against various joints and body parts of a human body. The ice-pack holder includes first and second flexible, elongated strap sections with first and second flexible, transverse strap sections secured between the first and second flexible, elongated strap sections. The first and second elongated strap sections and the first and second transverse strap sections define a central support section which covers an upper surface of an ice-bag or like device. Looped sections of fastener material are further secured to upper portions of the first and second elongated strap sections while a plurality of independent, hooked sections of fastening material are secured to the lower portions of the first and second elongated strap sections. The first and second elongated straps are articulated around a joint or body part in a circular fashion whereby the hooked sections of fastening material are operable to engage with the looped sections of fastening material to hold the ice-pack or like device securely in place. The ice-pack holder may be applied or removed quickly, easily and efficiently with a minimum amount of of discomfort to the wearer.

10 Claims, 2 Drawing Sheets

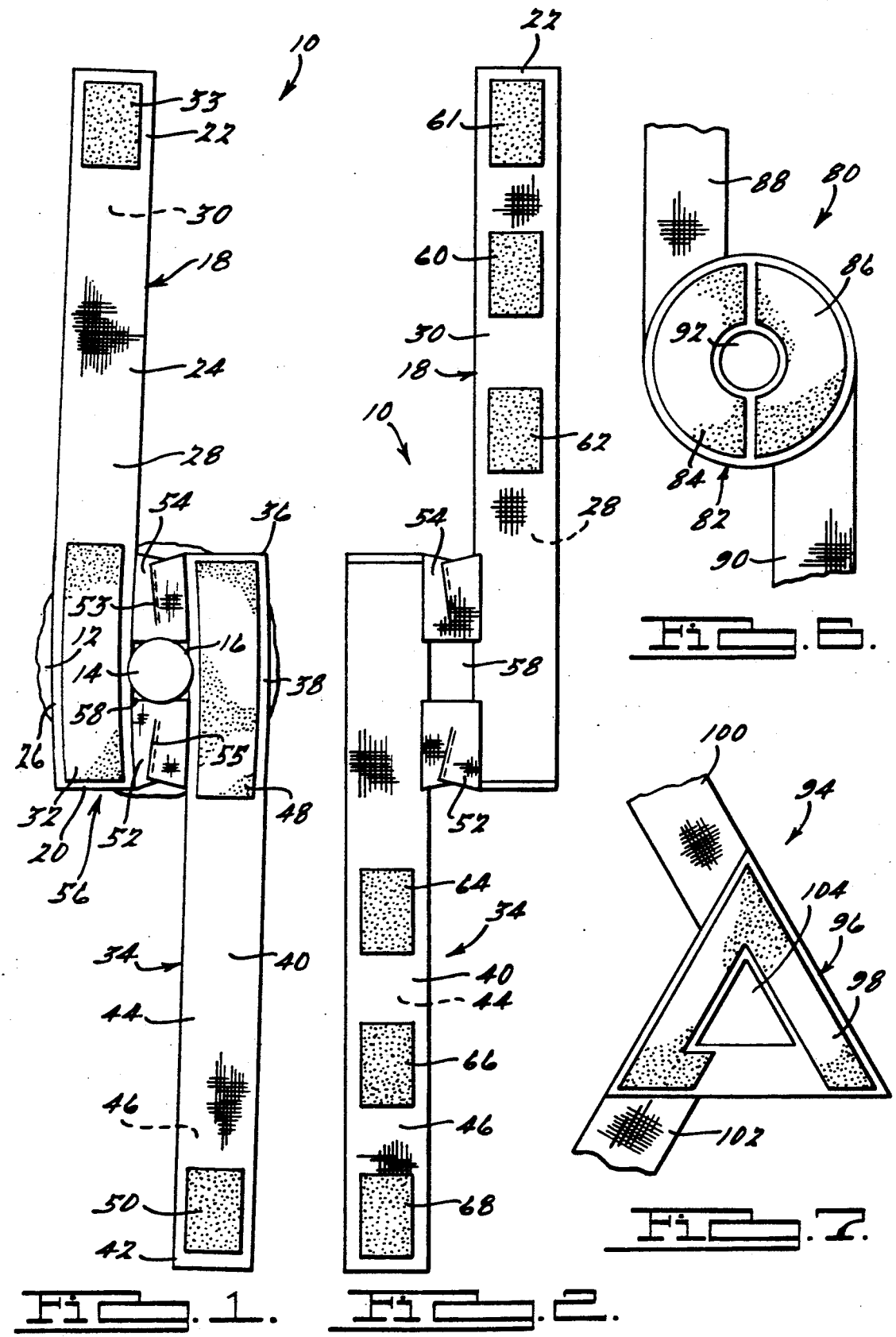

UNIVERSAL ICE-PACK HOLDER FOR APPLICATION TO JOINTS AND MUSCLES

BACKGROUND OF THE INVENTION

1. Technical Field

This invention relates generally to flexible strapping mechanisms and, more particularly, to a flexible support device for removably securing an ice-pack to various joints and muscles of a human body.

2. Discussion

Ice-packs or hot-water containers are often used by athletes and non-athletes to reduce swelling and remove soreness from various joints or other areas of the human body, or such swelling or soreness as the result of muscular injury, or muscular inflammation or even arthritis. Securing an ice-pack or hot-water container to a traumatized joint for various periods of time often helps to alleviate the discomfort, swelling and/or soreness associated with such muscular injuries or other degenerative conditions.

When an ice-pack or hot-water container is intended to be applied to a particular joint or muscle for various periods of time, it becomes necessary to incorporate some means for securing the ice-pack or hot-water container securely against the inflamed or sore joint or muscle. Heretofore, this has commonly been accomplished by various types of tape, strapping and bandages which are adapted to be wrapped around the ice-pack or hot-water container and areas of the affected joint or muscle to thereby hold the ice-pack or hot-water container securely against the joint or muscle. Typically, such devices have proved to be time consuming and/or inconvenient to secure to the various joints of the human body. This becomes a particular drawback with athletes who incur minor injuries during sporting events. In such cases ice-packs are often periodically applied to the injured joint of an athlete during intermissions, half-times, etc., when an athlete is temporarily resting. When the athlete must periodically enter and exit a game or other event, the tape, bandage, etc., securing an ice-pack to an injured joint or muscle often has to be quickly removed or applied, while causing only a minimum of discomfort to the athlete.

Present devices for the above-described purpose often impede the quick and/or periodic application or removal of an ice-pack. Bandages are often wrapped around a limb or joint several times, with multiple bandages often being required to secure an ice-pack to various parts of the human body such as the shoulders. Such devices are therefore of limited value to athletes, in particular, where ice-packs, hot-water containers, etc., must be applied and removed periodically in a quick and efficient manner.

It is therefore a principal object of the present invention to provide a universal ice-pack holder operable to quickly and efficiently secure an ice-pack, hot-water container, etc., to a joint or muscle area of the human body.

It is a further object of the present invention to provide a universal ice-pack holder which may be used to secure an ice-pack, hot-water container, etc., to virtually any joint or muscle area of the human body in a quick and efficient manner.

It is still a further object of the present invention to provide a universal ice-pack holder which is comfortable to wear in contact with the skin for prolonged periods of time while reducing the risk of rashes or other forms of skin irritation.

It is yet another object of the present invention to provide a universal ice-pack holder for securing an ice-pack, hot-water container, etc., to a joint or muscle area of the human body, which is of a relatively simple and inexpensive construction.

It is still a further object of the present invention to provide a universal ice-pack holder which is manufactured of materials which stretch and generally conform to the shapes of various limbs of a human body, thereby enhancing the comfort of the ice-pack holder.

SUMMARY OF THE INVENTION

The above and other objects are provided by an ice-pack holder in accordance with the present invention. The ice-pack holder generally comprises a central support section which includes a plurality of elongated, oppositely extending, flexible straps. Secured to portions of the central support section is a first fastening material. The central support section is adapted to be secured over a substantial portion of an ice-pack, hot-water container, etc., and to hold the ice-pack or like device securely against a joint or muscle of the human body. An outermost end of each elongated strap further includes at least a first section of a second fastening material.

The first and second elongated straps are adapted to be wrapped around portions of a limb which includes the affected joint or muscle area. The first fastening materials are adapted to detachably couple with the first sections of fastening material to thereby hold the ice-pack or a like device securely against the affected joint or muscle.

In a first preferred embodiment of the present invention the first and second sections of fastening materials comprise mating strips of Velcro fastening material or a similar material. The ice-pack holder of the present invention is adapted to be quickly, easily and efficiently applied and removed to virtually any joint or muscle of the human body with little or no discomfort to a wearer.

BRIEF DESCRIPTION OF THE DRAWINGS

The various advantages of the present invention will become apparent to one skilled in the art by reading the following specification and subjoined claims and by referencing the following drawings in which:

FIG. 1 is a plan view of an ice-pack holder in accordance with the present invention;

FIG. 2 is a plan view of an undersurface of the ice-pack holder of the present invention;

FIG. 6 is a first alternative preferred embodiment of the present invention; and FIG. 7 is a second alternative preferred embodiment of the present invention.

DETAILED DESCRIPTION OF THE PREFERRED EMBODIMENTS

Figure 3:
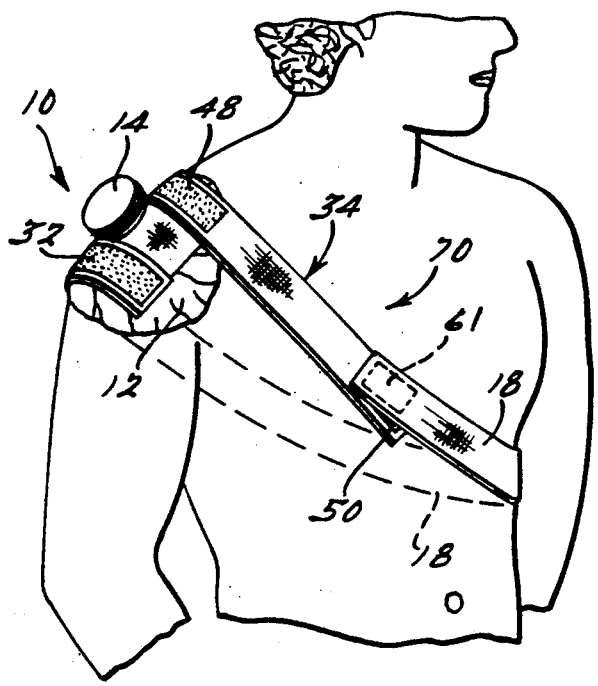
FIG. 3 is an illustration of the ice-pack holder of the present invention secured over a shoulder of a wearer.

Referring now to FIG. 1, an ice-pack holder 10 in accordance with the present invention is shown. An ice-pack 12 having a cap 14 and a neck portion 16 (shown more clearly in FIGS. 3-5) is also illustrated. The ice-pack holder 10 generally comprises a first elastic, elongated strap 18 having a first end 20, a second end 22, an intermediate section 24 and a central support portion 26. In addition, the first strap 18 includes an upper surface 28 and a lower surface 30 (shown more clearly in FIG. 2). The upper surface 28 of the first strap 18 includes a first elongated strip of looped fastening material 32 affixed to the first end and central support portion 20 and 26 respectively of its upper surface 28. A second strip of looped fastening material 33 is further secured to the second end 22 of the elastic strap 18. In a preferred embodiment of the present invention the looped fastening material 32 and 33 each comprise sections of Velcro fastening material which are preferably stitched around their perimeters to the elastic strap 18. Adhesives or other fastening means, however, could alternatively be used to secure fastening materials 32 and 33.

A second elastic, elongated strap 34 is also included which has a first end 36, a central support portion 38, an intermediate section 40, and a second end 42, as well as upper and lower surfaces 44 and 46 respectively. The second strap 34 further includes a second elongated strip of looped fastening material 48 secured to its first end portion and central support section 36 and 38 respectively. Secured to its second end portion 42 is a second section of looped fastening material 50. Fastening materials 48 and 50 are preferably secured to the second strap 34 by stitching around their perimeters, although adhesives or other means of attachment could just as easily be employed.

Disposed inbetween the central support portions 26 and 38 of the first and second straps 18 and 34 respectively is a first elastic, transverse strap section 52 and a second elastic, transverse strap section 54. The transverse strap sections 52 and 54 are preferably stitched to the central support portions 26 and 38 of the first and second straps 18 and 34 respectively. Transverse strap sections 52 and 54 also each include stitched portions 53 and 55 respectively, which help the strap sections 52 and 54 to more formably rest over ice-pack 12 when the ice pack holder 10 is secured over the ice-pack 12. Together, the central support portions 26 and 38 of straps 18 and 34 along with the transverse straps 52 and 54 form a single piece, integral, central support section 56 having a central, generally square-shaped opening 58 through which the neck portion 16 of the ice-pack 12 may extend. The central support section 56 preferably substantially covers the ice-pack 12 to ensure maximum surface area contact of the ice-pack with the joint or other body portion which it contacts. As can also be seen from the drawing of FIG. 1, the flexible, elastic nature of the straps 18, 34, 52 and 54 enables the central support section 56 to conform to a concave shape over the ice-pack 12 when the ice-pack 12 is filled with ice. Opening 58 also enables the cap 14 of the ice-pack 12 to be removed, thus permitting ice to be added or removed from the ice-pack 12 without removing the ice-pack holder 10 from the joint or other body part which it is secured to.

Referring now to FIG. 2, the ice-pack holder 10 can be seen from its reverse side. From FIG. 2 it can be seen that the lower surfaces 30 and 46 of the first and second strap sections 18 and 34 further include a plurality of sections of hooked fastening material 60, 61, 62, 64, 66 and 68. The hooked sections of fastening material 60-68 are also secured to the first and second straps 18 and 34 by stitching, although adhesives or other means of attachment could be used.

In a preferred embodiment of the present invention the hooked strips of fastening material 60, 61, 62, 63, 64, 65, 66, 67 and 68 each comprise hooked sections of Velcro fastening material. The hooked sections of fastening material 60-68 are generally operable to detachably couple with the looped sections of fastening material 32 and 48 shown in FIG. 1 when the ice-pack holder 10 is holding the ice-pack 12 against a joint or other body part.

Figure 4:
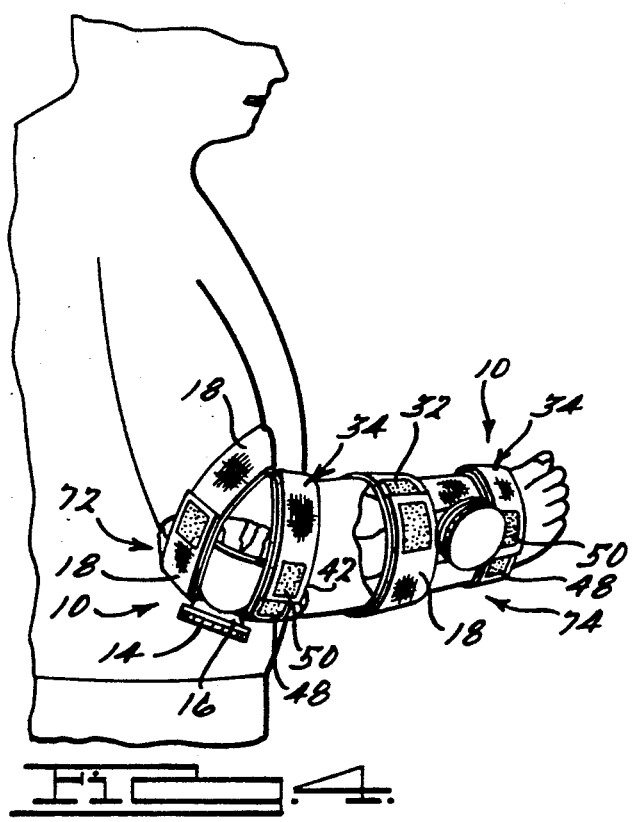
FIG. 4 illustrates the ice-pack holder of the present invention secured to elbow and wrist portions of an arm.
Figure 5:
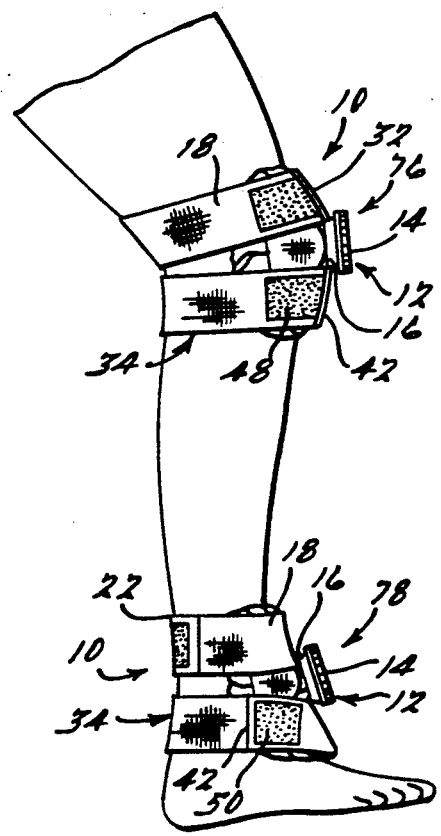
FIG. 5 illustrates the ice-pack holder of the present invention secured to knee and ankle portions of a leg.

Referring now to FIGS. 1 and 2, and as will become more apparent from FIGS. 3-5, hooked fastening sections 60, 61 or 62, or a combination thereof, are typically coupled with looped fastening section 32 by wrapping the first strap 18 around a portion of the limb having the affected joint. As the first strap 18 circumscribes a portion of the limb the hooked sections of fastening material 60, 61 and 62 are articulated into a position where they lie above the elongated section of looped fastening material 32. Coupling of any one of the hooked fastening sections of material 60, 61 or 62, or a combination thereof, is accomplished by simply pressing the surfaces of sections 60, 61 or 62 into contact with looped fastening material 32. To detach the hooked fastening sections 60, 61 or 62, the second end 22 of first strap 18 is simply peeled off of and away from, along with the intermediate section 24 of first strap 18, the upper surface 28 of central support portion 26. The attachment and removal of second strap 34 may be effected in a similar fashion with looped fastening material 48.

By providing a plurality of hooked fastening sections of material 60-68, the first and second straps 18 and 34 may be adjusted to accommodate a variety of limb thicknesses and yet maintain a secure coupling between one or a combination of the hooked fastening sections 60-68 and the looped sections of fastening material 32 and 48. In this manner, each strap 18 and 34 may be adjusted to accommodate securing the ice-pack holder 10 to a wrist joint, ankle joint, knee joint, or even over a hip portion, where each such area of the body or of a particular limb would have a different diameter.

Referring now to FIG. 3, the ice-pack 12 is shown attached to a shoulder portion of an upper torso. From FIG. 3 it can be seen that looped fastening section 50 (shown in FIG. 1) on second strap 34 enables the second strap 34 to be coupled with the second end 22 of first strap 18 when the full lengths of straps 18 and 34 are needed to properly secure the ice-pack holder 10 to a joint. As the second strap 34 is placed over the chest area 70 of a person, the first strap 18 is brought around behind the person and against the back until it wraps around to the chest area 70 of the wearer. Fastening sections 50 and 61 may then be coupled together simply by pressing them against each other.

Referring now to FIG. 4, the ice-pack holder 10 is shown applied to the elbow 72 and wrist 74 portions of an arm. When attached to the elbow portion 72, it can be seen how straps 18 and 34 wrap around portions of the arm to hold the ice-pack 12 securely in place. In FIG. 5, the ice-pack holder 10 is shown securing the ice-pack 12 to knee 76 and ankle 78 portions of a human leg in a similar fashion.

In FIG. 6, an alternative preferred embodiment 80 of the present invention is shown. This embodiment generally comprises a circular central support section 82 having first and second looped fastening sections of material 84 and 86 secured thereto. Extending in opposite directions from the central support section 82 are first and second straps 88 and 90. Further included in the central support section 82 is an annular opening 92 through which the neck 16 of water bottle 12 may protrude when it is secured by the ice-pack holder 80 to a joint or muscle area.

In FIG. 7 a second alternative preferred embodiment 94 is shown which comprises a generally triangularly-shaped central support portion 96, a generally triangularly-shaped looped fastening material 98 secured thereto, and first and second straps 100 and 102 secured to the central support section 96. The central support portion 96 further includes a triangularly-shaped opening 104 through which the neck 16 of the ice-pack 12 may protrude when the ice-pack 12 is secured by the ice-pack holder 94 to a joint.

While the ice-pack holder 10 of the present invention has been shown applied to shoulder, elbow, wrist, knee and ankle areas of a human body, it should be appreciated that the invention could just as easily be applied to virtually any other area of the body where muscular soreness, inflammation or pain exists. For example, the ice-pack holder 10 could just as easily be applied to the bicep, a rib area of the upper torso, the back area of the upper torso, a quadracep, hamstring, or calf.

Those skilled in the art can now appreciate from the foregoing description that the broad teachings of the present invention can be implemented in a variety of forms. Therefore, while this invention has been described in connection with particular examples thereof, the true scope of the invention should not be so limited since other modifications will become apparent to the skilled practitioner upon a study of the drawings, specification and following claims.

What is claimed is:

1. An apparatus for securing a therapeutic device to various areas of a human body, comprising:

central support means adapted to removably support and secure said therapeutic device in abutting contact with a desired area of said human body;

said central support means having at least first and second elongated, strap means each having inner and outer ends, said outer ends of said first and second strap means extending outwardly of said central support means in generally opposite directions for further helping to removably secure said therapeutic device in abutting contact with said desired area of said human body;

said central support means further having an opening adapted to engage a portion of said therapeutic device to thereby further help removably secure said theraputic device to said desired area of said human body;

said opening in said central support means further being disposed inbetween and adjacent said inner ends of said first and second strap means, wherein said first and second strap means extend along generally parallel paths from opposite sides of said opening; and fastening means for fastening said outer end portion of each said first and second elongated strap means with each other or with portions of said central support means after said elongated strap means have been secured against said desired area of said human body, whereby said fastening of each elongated strap means to said central support means causes said central support means to hold said therapeutic device securely against said desired area of said human body.

2. The apparatus of claim 1, wherein said central support means further comprises third and fourth strap means for further helping to secure said therapeutic device against said desired portion of said human body, said third and fourth strap means further each being secured to said first and second strap means, whereby said first, second, third and fourth strap means operate cooperatively to provide an integral central support structure for holding said therapeutic device securely against said desired part of human body.

3. The apparatus of claim 1, wherein said fastening means comprises:

a plurality of looped fasteners secured to said central support section; and a plurality of detachable hooked fasteners secured to portions of said first and second elongated, oppositely facing strap means, said hooked fasteners being operable to couple with said looped fasteners to thereby secure said end portions of said first and second elongated, oppositely facing strap means with said central support means.

4. The apparatus of claim 1, wherein said first and second elongated, oppositely facing strap means and said central support means comprise integrally formed elastic straps.

5. The apparatus of claim 1, wherein said opening in said central support means comprises an opening formed centrally in said central support means for enabling a portion of said therapeutic device to protrude therethrough, thereby facilitating secure, removable placement of said therapeutic device.

6. A universal ice-pack holder adapted to secure an ice-pack to an area of a human body, comprising:

first flexible, elongated strap means having inner and outer ends for circumscribing a first portion of said area and further helping to secure said ice-pack to said area;

second flexible, elongated strap means having inner and outer ends for circumscribing a second portion of said area and further helping to secure said ice-pack to said area;

first and second transverse strap means disposed intermediate said first and second flexible, elongated strap means and secured to said first and second flexible, elongated strap means for further helping to secure said ice-pack to said area, said first and second flexible, elongated strap means and said first and second transverse strap means forming an integral, central support section having a centrally disposed opening therein;

said outer ends of said first and second flexible, elongated strap means extending outwardly of said central support section in opposite directions thereof and generally parallel to each other, said flexible, elongated strap means further extending outwardly from opposite sides of said centrally disposed opening;

a plurality of first fastening means associated with said central support section for helping to secure said ice-pack to said area; and a plurality of second fastening means disposed on portions of said flexible, elongated first and second strap means for removably fastening with said first fastener means after said flexible, elongated strap means are positioned around said area, said first and second fastening means thereby operating cooperatively to removably secure said ice-pack against said area.

7. The ice-pack holder of claim 6, wherein said first and second flexible, elongated strap means and said first and second transverse strap means each comprise elastic straps operable to substantially follow a contour of said ice-pack and said area when said ice-pack holder is securing said ice-pack to said area.

8. The ice-pack holder of claim 6, wherein each said first fastening means comprises an elongated strip of fastening material having a large plurality of hook portions protruding therefrom, each said elongated section of fastening material being securely affixed to its associated first strap means, and wherein said second fastening means comprises a plurality of looped surface fastening materials secured to end portions of said flexible, elongated first and second strap means, said looped surface fastening materials and said hook surface fastening materials being operable to removably couple portions of said first and second flexible, elongated strap means with said elongated strips of fastening material having hooked portions, thereby securing said flexible, elongated first and second strap means around said area and with said central support section to thereby secure said ice-pack to said area.

9. The ice-pack holder of claim 8, wherein said sections of said hooked surface fastening material and said looped surface fastening material are stitched to said first and second flexible, elongated strap means.

10. A universal ice-pack holder adapted to hold an ice-pack having a neck portion securely to an area of a human body, comprising:
- a first elastic, elongated strap having first and second end portions and an intermediate portion;
- a second, elastic, elongated strap having first and second end portions and an intermediate portion;
- a first elastic, transverse strap disposed inbetween and coupled to said first end of said first elastic, elongated strap and said intermediate portion of said second elastic, elongated strap;
- a second elastic, transverse strap disposed inbetween and coupled with said intermediate portion of said first elastic, elongated strap and said first end portion of said second elastic, elongated strap, said first and second elastic, elongated straps and said first and second elastic, transverse straps thereby forming a central support section having a generally square-shaped opening, said generally square-shaped opening being operable to allow said neck portion of said ice-pack to protrude therethrough;
- said second end portions of said first and second elastic, elongated straps extending outwardly of said central support section in generally opposite directions, said first and second elastic, elongated straps further extending outwardly in generally parallel fashion from opposite sides of said generally square-shaped opening;
- a first elongated strip of fastening material having a hooked surface stitched to said first end portion and said intermediate portion of said first elastic, elongated strap;
- a second elongated strip of fastening material having a hooked surface stitched to said first end portion and said intermediate portion of said second elastic, elongated strap;
- at least a first strip of fastening material having a looped surface stitched to said second end portion of said first elastic, elongated strap, said first strip of fastening material being operable to detachably couple with said hooked surface of said first elongated strip of fastening material; and
- a second section of fastening material having a looped surface, said second section of fastening material being secured at said second end portion of said second elastic, elongated strap, said looped surface of said second strip of fastening material being operable to detachably couple with said hooked surface of said second elongated strip of fastening material, whereby said detachable coupling of said first strip of fastening material having said hooked surface and said first fastening material having said looped surface, and said detachable coupling of said hooked surface of said second strip of fastening material and said looped surface of said second strip of fastening material operate cooperatively to help removably secure said ice-pack and to said area of said human body.

* * * * *